US007021310B1

(12) United States Patent
Sinderby et al.

(10) Patent No.: US 7,021,310 B1
(45) Date of Patent: Apr. 4, 2006

(54) PROPORTIONAL PRESSURE ASSIST VENTILATION CONTROLLED BY A DIAPHRAGM ELECTROMYOGRAPHIC SIGNAL

(75) Inventors: Christer Sinderby, Montreal (CA); Jennifer Beck, Montreal (CA)

(73) Assignee: Universite De Montreal, Montreal (CA)

( * ) Notice: Subject to any disclaimer, the term of this patent is extended or adjusted under 35 U.S.C. 154(b) by 0 days.

(21) Appl. No.: 09/701,824

(22) PCT Filed: Jun. 4, 1999

(86) PCT No.: PCT/CA99/00529

§ 371 (c)(1),
(2), (4) Date: May 31, 2001

(87) PCT Pub. No.: WO99/62580

PCT Pub. Date: Dec. 9, 1999

(30) Foreign Application Priority Data

Jun. 4, 1998 (CA) .................................... 2239673

(51) Int. Cl.
*A61M 16/00* (2006.01)
*A62B 7/00* (2006.01)
*F16K 31/02* (2006.01)

(52) U.S. Cl. ......................... 128/204.23; 128/204.18; 128/204.21; 128/925; 600/587; 600/546

(58) Field of Classification Search ........... 128/204.18, 128/204.21, 204.23, 204.26, 200.14, 925; 600/925, 587, 593, 546, 547
See application file for complete search history.

(56) References Cited

U.S. PATENT DOCUMENTS

| 3,905,355 A | | 9/1975 | Brundy | |
|---|---|---|---|---|
| 3,961,627 A | * | 6/1976 | Ernst et al. | 128/204.23 |
| 3,972,327 A | * | 8/1976 | Ernst et al. | 128/204.23 |
| 4,867,152 A | * | 9/1989 | Kou et al. | 128/204.21 |
| 4,986,268 A | * | 1/1991 | Tehrani | 128/204.22 |
| 5,044,362 A | * | 9/1991 | Younes | 128/204.21 |
| 5,107,830 A | * | 4/1992 | Younes | 128/204.18 |
| 5,129,390 A | * | 7/1992 | Chopin et al. | 128/204.21 |
| 5,134,995 A | * | 8/1992 | Gruenke et al. | 128/204.23 |
| 5,353,788 A | | 10/1994 | Miles | |

(Continued)

FOREIGN PATENT DOCUMENTS

EP 0776671 A1 6/1997

(Continued)

OTHER PUBLICATIONS

"Electromyography Of The Diaphragm In Man And Transdiaphragmatic Pressure", Agostoni et al., Journal of Applied Physiology, vol. 15, 1960 pp. 1093-1097.

(Continued)

*Primary Examiner*—Henry Bennett
*Assistant Examiner*—Dinnatia Doster-Greene
(74) *Attorney, Agent, or Firm*—Perman & Green, LLP.

(57) ABSTRACT

A closed loop system uses (a) the intensity of the diaphragm electromyogram (EMG) for a given inspiratory volume; (b) the inspiratory volume for a given EMG intensity; or (c) a combination of (a) and (b); in view of controlling the level of gas flow, gas volume or gas pressure delivered by a mechanical (lung) ventilator. The closed loop ventilator system enables for automatic or manual adjustment of the level of inspiratory support in proportion to changes in the neuro-ventilatory efficiency such that the neural drive remains stable at a desired target level. An alarm can also be used to detect changes in neuroventilatory efficiency in view of performing manual adjustments.

26 Claims, 10 Drawing Sheets

U.S. PATENT DOCUMENTS

| | | | |
|---|---|---|---|
| 5,520,192 A * | 5/1996 | Kitney et al. | 600/529 |
| 5,535,738 A * | 7/1996 | Estes et al. | 128/204.23 |
| 5,549,655 A * | 8/1996 | Erickson | 607/42 |
| 5,582,163 A * | 12/1996 | Bonassa | 128/204.26 |
| 5,671,752 A | 9/1997 | Sinderby et al. | |
| 5,720,278 A * | 2/1998 | Lachmann et al. | 128/204.23 |
| 5,794,615 A * | 8/1998 | Estes | 128/204.23 |
| 5,820,560 A * | 10/1998 | Sinderby et al. | 600/546 |
| 5,878,744 A * | 3/1999 | Pfeiffer | 128/204.23 |
| 5,884,622 A * | 3/1999 | Younes | 128/204.21 |
| 5,915,381 A * | 6/1999 | Nord | 128/204.23 |
| 5,931,162 A * | 8/1999 | Christian | 128/204.23 |
| 5,953,713 A * | 9/1999 | Behbehani et al. | 706/16 |
| 6,015,388 A * | 1/2000 | Sackner et al. | 600/529 |
| 6,041,780 A * | 3/2000 | Richard et al. | 128/204.18 |
| 6,158,432 A * | 12/2000 | Biondi et al. | 128/204.21 |
| 6,411,843 B1 * | 6/2002 | Zarychta | 600/546 |
| 6,588,423 B1 * | 7/2003 | Sinderby | 128/204.23 |
| 6,920,875 B1 * | 7/2005 | Hill et al. | 128/204.18 |
| 6,920,878 B1 * | 7/2005 | Sinderby et al. | 128/204.23 |
| 2003/0188748 A1 * | 10/2003 | Sinderby et al. | 128/204.21 |

FOREIGN PATENT DOCUMENTS

| | | |
|---|---|---|
| WO | WO 96/11717 | 4/1996 |
| WO | WO 97/16216 | 5/1997 |
| WO | WO 97/22377 | 6/1997 |
| WO | WO 97/28838 | 8/1997 |
| WO | WO 98/48877 | 11/1998 |

OTHER PUBLICATIONS

Beck et al., J Appl Physiol. Sep. 1996;81(3):1434-1449.

* cited by examiner

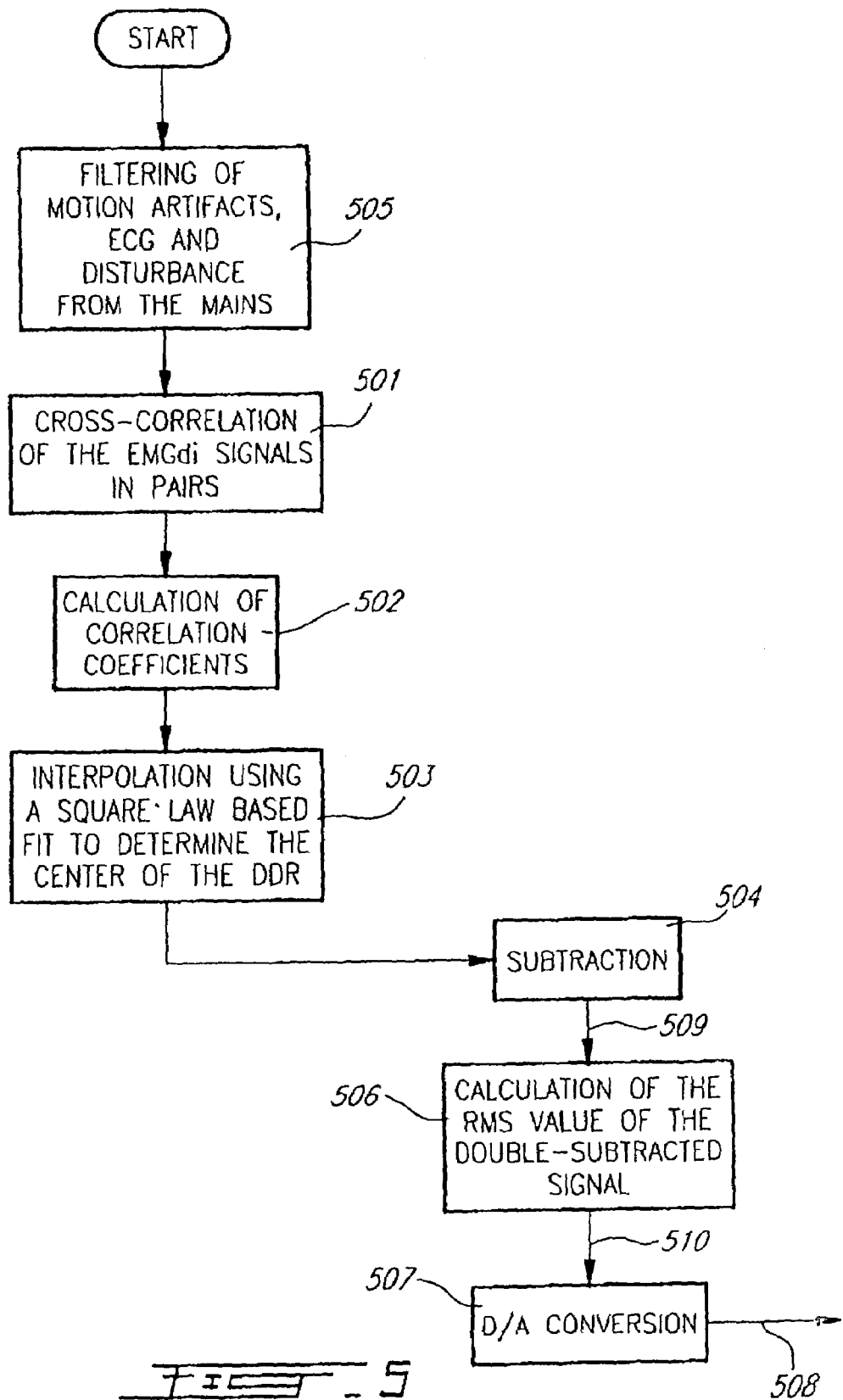

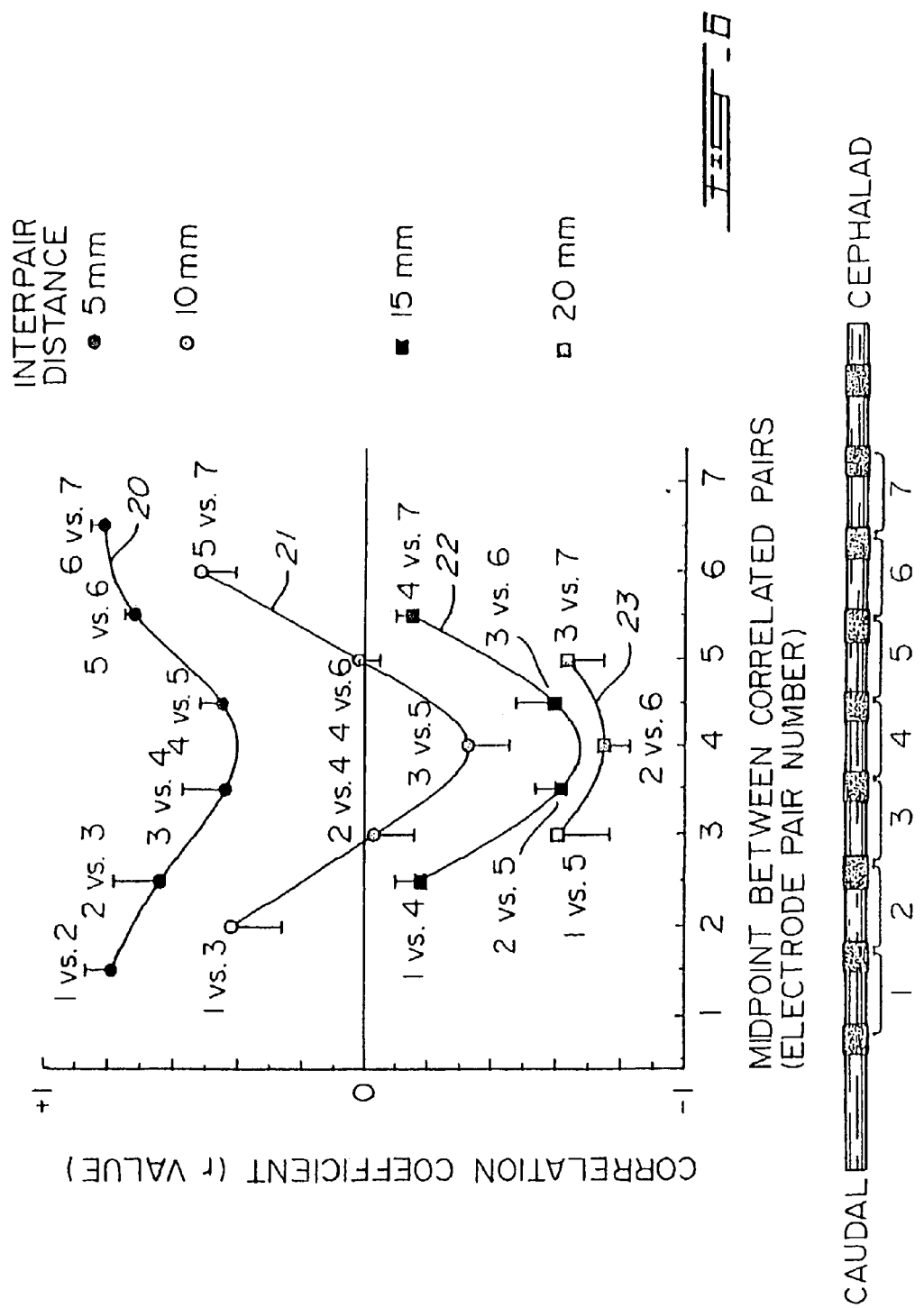

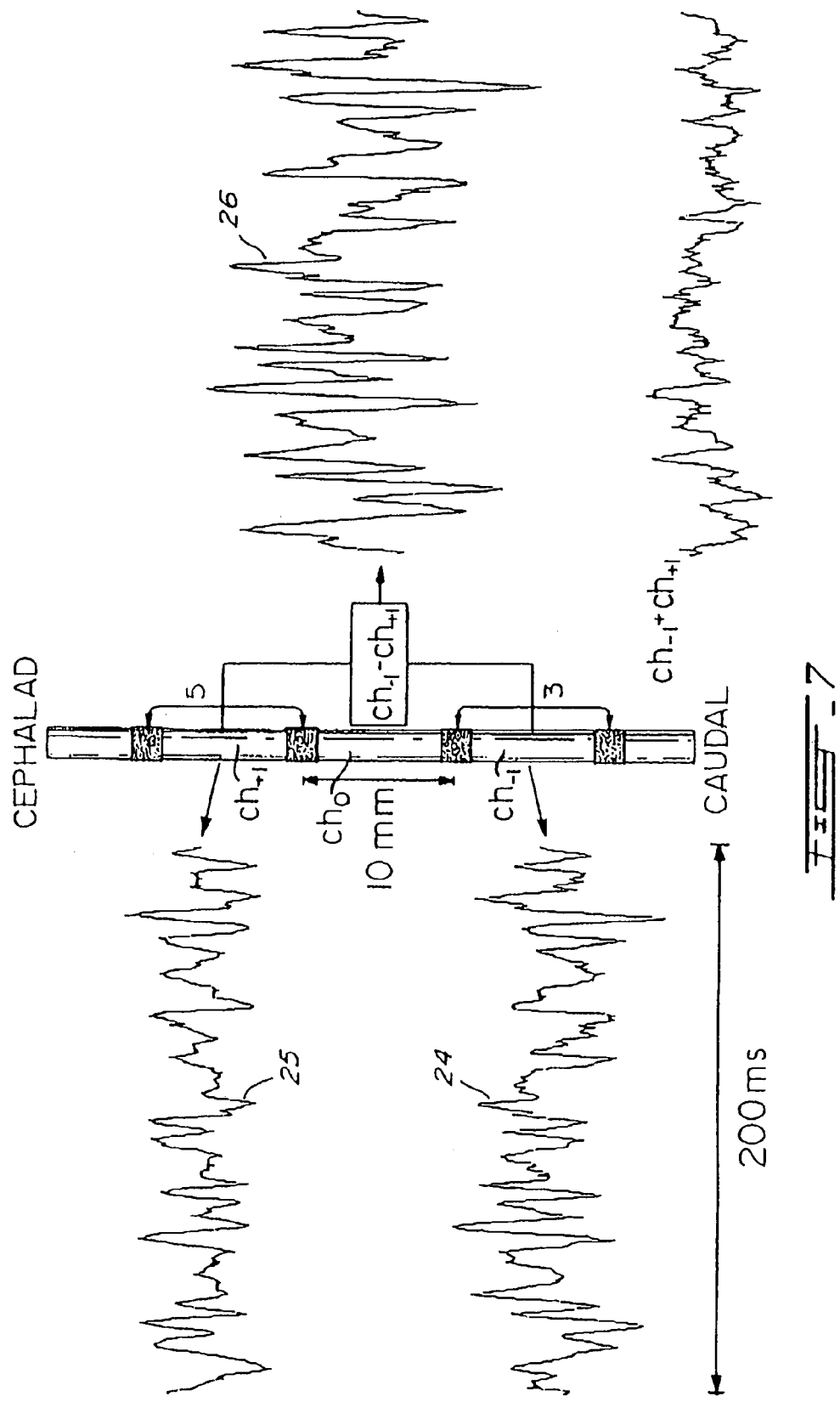

PROPORTIONAL PRESSURE ASSIST VENTILATION CONTROLLED BY A DIAPHRAGM ELECTROMYOGRAPHIC SIGNAL

BACKGROUND OF THE INVENTION

1. Field of the Invention

The present invention relates to a system using the intensity of the diaphragm electromyogram (EMG) at a given lung volume or the lung volume at a given EMG intensity to automatically or manually adjust the level of inspiratory support in proportion to changes in the neuro-ventilatory efficiency.

The present invention also relates to a system responsive to the intensity of the diaphragm electromyogram (EMG) measured immediately before the onset of inspiratory flow to automatically or manually control and maintain an optimum level of extrinsic positive end expiratory pressure (PEEP) applied to a patient, and to automatically or manually control a duration from the onset of EMG to onset of respiratory flow.

2. Brief Description of the Prior Art

Prior art algorithms used to create closed-loop ventilator systems are based on variables such as tidal volume, respiratory rate, inspiratory flow, end-tidal carbon dioxide levels and/or rate of rise in pressure. However, none of these parameters can provide a reliable measure of the respiratory neural drive because they are affected by changes in neuro-mechanical or neuro-ventilatory efficiency.

Neuro-ventilatory efficiency is a term used to express the amount of neural drive (breathing effort) needed to obtain a given tidal lung volume. In brief, neural drive is converted into mechanical tension, a process which is influenced by the muscle length, temperature, electrolyte imbalance, etc. The role of inspiratory flow in the link between neural drive and mechanical tension has previously been suggested; however the proposed influence could not be demonstrated for mean inspiratory flow rates up to 1.4 liters/second. The mechanical tension is then translated into pressure. a process which is affected by the shape of the diaphragm dome. Finally the pressure expands the alveoli and causes air to flow, and the translation of pressure to volume depends on the elasto-viscous behaviour of the respiratory system. Consequently, there are many factors that may influence the tidal volume output obtained for a given increase in neural drive (inspiratory effort).

Evaluation of respiratory drive by measurements such as the rate of rise in pressure or lung volume is not reliable when, for example, the muscle length or the respiratory system impedance are affected by changes in the neuro-ventilatory efficiency. In a patient, airway resistance and elastance can change from one minute to another and muscle length is continuously altered.

OBJECTS AND SUMMARY OF THE INVENTION

An object of the present invention is therefore to eliminate the drawbacks of the prior art.

Another object of the present invention is to provide a closed loop system using:

(a) the intensity of the diaphragm electromyogram (EMG) for a given inspiratory volume;
(b) the inspiratory volume for a given EMG intensity; or
(c) a combination of (a) and (b);

in view of controlling the level of gas flow, gas volume or gas pressure delivered by a mechanical (lung) ventilator; the closed loop ventilator system enables for automatic or manual adjustment of the level of inspiratory support in proportion to changes in the neuro-ventilatory efficiency such that the neural drive remains stable at a desired target level. An alarm can also be used to detect changes in neuroventilatory efficiency in view of performing manual adjustments.

Another object of the present invention is to provide a closed-loop system responsive to the intensity of the diaphragm EMG measured immediately before the onset of inspiratory flow to quantify pre-inspiratory breathing effort in view of automatically or manually adjusting a level of extrinsic positive end expiratory pressure (PEEP) applied to a patient in proportion to changes in EMG intensity of pre-inspiratory efforts. In this manner, the pre-ventilatory intensity of the diaphragm EMG can be maintained at a desired, minimum level such that the pre-inspiratory neural drive remains stable at a desired target minimal level. Determination of the duration from the onset of EMG to the onset of respiratory flow is also used for quantitative evaluation of the intrinsic PEEP, and to guide adjustment of the trigger sensitivity of the ventilator systems.

Different from pressure and ventilatory related indexes, the intensity of the EMG represents the temporal (mean MU (motor unit) rate coding) and spatial (MU recruitment) summation of action potentials and is obtained at the level of the sarcolemma muscle. The intensity of the EMG is therefore not affected by changes in the muscle's neuro-ventilatory coupling. In the present invention, the use of crural diaphragm EMG rests on the assumption that neural drive to the crural diaphragm is representative for the total respiratory drive. It is also based on the condition that neuromuscular transmission and innervation of the crural diaphragm are normal. For breathing with increased demand this assumption is well founded. Hence, the intensity of the EMG needed to produce a given inspiratory volume should express the efficiency relation between neural drive and volume output.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 5 is a flow chart showing a method for conducting a double subtraction technique of the EMGdi signals;

FIG. 6 is a graph showing the distribution of correlation coefficients calculated for determining the position of the center of the depolarizing region of the diaphragm along the array of electrodes of FIG. 2;

FIG. 7 is a schematic diagram illustrating in the time domain a double subtraction technique for improving the signal-to-noise ratio and to reduce an electrode-position-induced filter effect along the array of electrodes of FIG. 2;

DETAILED DESCRIPTION OF THE PREFERRED EMBODIMENT

Although the preferred embodiment of the present invention will be described in relation to a double subtracted EMGdi signal, it should be kept in mind that the concept of the present invention can be used with any respiratory muscle signal.

Figure 1:
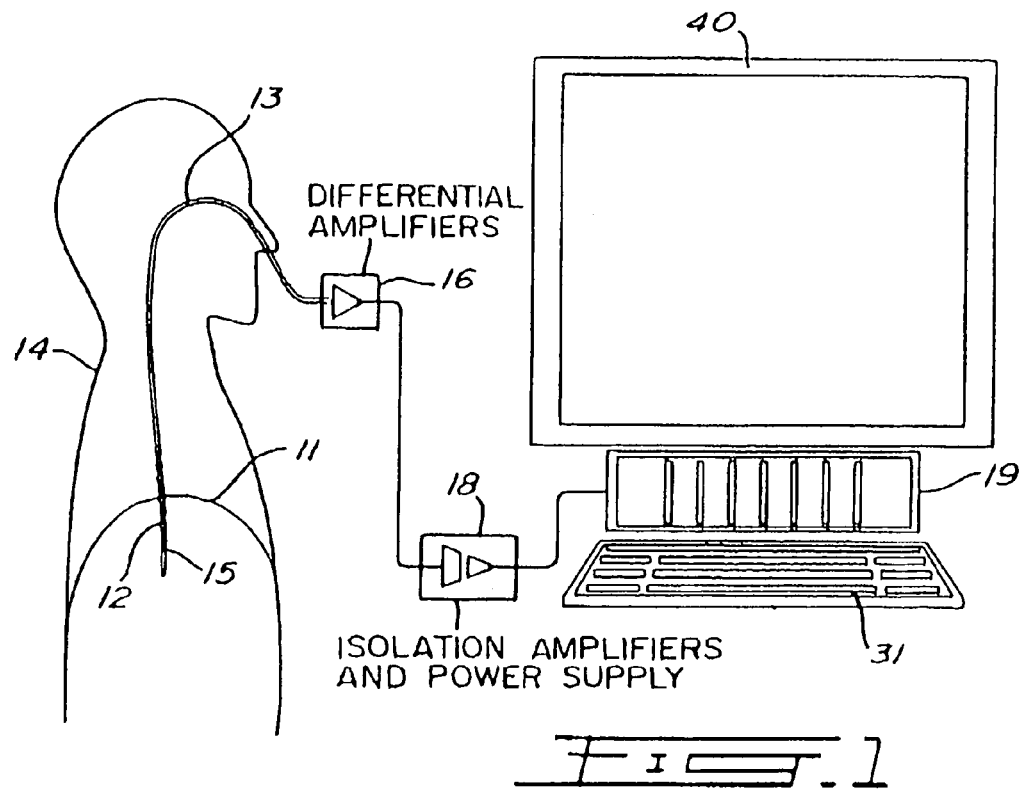
FIG. 1 is a schematic representation of a set-up of an EMG analysis system.
Figure 2:
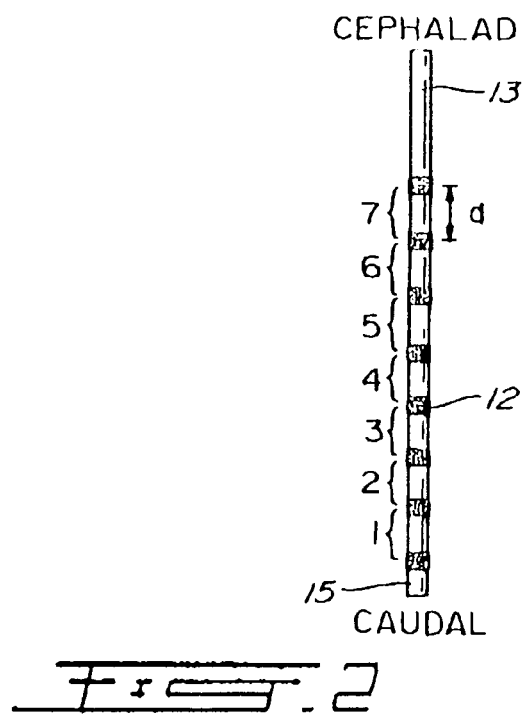
FIG. 2 is a section of oesophageal catheter on which an array of electrodes of the EMG analysis system of FIG. 1 is mounted.

To measure EMG activity of the diaphragm 11 (EMGdi) of a human patient 14, an array of electrodes such as 12 (FIGS. 1 and 2) are mounted on the free end section 15 of an oesophageal catheter 13, with a constant inter-electrode distance d (FIG. 2). As shown in FIG. 1, the catheter 13 is introduced into the patient's oesophagus through one nostril or the mouth until the array of electrodes 12 is situated at the level of the gastroesophageal junction. The diaphragm 11 and/or the oesophagus slightly move during breathing of the patient 14 whereby the array of electrodes 12 also slightly moves about the diaphragm 11. As will be explained in the following description, autorhatic compensation for this displacement is provided for.

According to a preferred embodiment, an electrode 12 is mounted on the free end section 15 of the catheter 13 by winding stainless steel wire (not shown) around that catheter 13. The wound stainless steel wire presents a rough surface smoothed out by solder, which in turn is electroplated with nickel, copper and then gold or silver. Of course, it is within the scope of the present invention to use other electrode structures. Also, the electrodes 12 can possibly be applied to a nasogastric feeding tube (not shown) which is routinely introduced in intensive-care unit (ICU) patients.

Electric wires (not shown) interconnect each pair of successive electrodes such as 1–7 (FIG. 2) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EMGdi signals collected by the various pairs 1–7 of electrodes 12 are shielded to reduce the influence of external noise, in particular disturbance from the 50 or 60 Hz current and voltage of the electrical mains.

The group of differential amplifiers 16 amplifies (first subtraction step of a so-called double subtraction technique) and band-pass filters each EMGdi signal. This first subtraction step may also be carried out in the personnal computer 19 when the amplifiers 16 are single-ended or equivalently designed amplifiers (monopolar readings).

Figure 3:
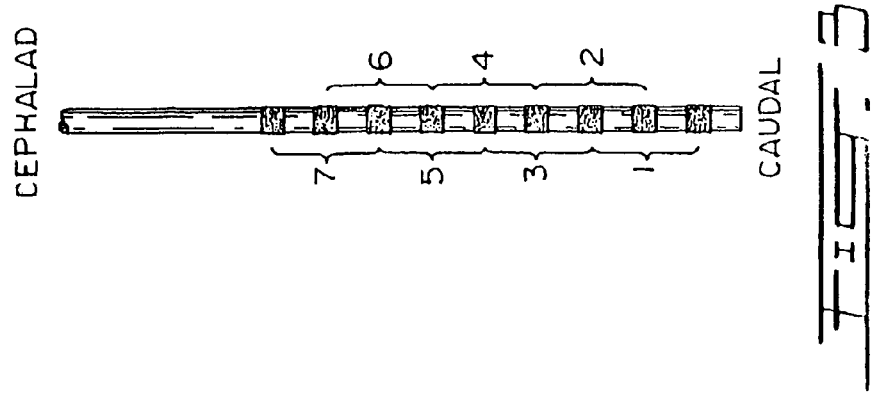
FIG. 3 illustrates a section of oesophageal catheter on which a second embodiment of the array of electrodes is mounted.

In the example illustrated in FIGS. 1 and 2, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that EMG activity of the diaphragm (EMGdi) can be measured accurately with an oesophageal catheter 13 provided on the free end section 15 thereof with an array of eight electrodes 12, a different number and/or configuration of pairs of electrodes 12 can be contemplated depending on the patient's anatomy and movement of the diaphragm. Also, the pairs 1–7 do not need to be pairs of successive electrodes; as an example FIG. 3 illustrates an array of nine electrodes to form seven overlapping pairs of electrodes 1–7.

A major problem in recording EMGdi signals is to maintain the noise level as low and as constant as possible. Signals the electric wires transmitting the EMGdi signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is preferably made as small as possible (miniaturized) and is positioned in close proximity to the patient to decrease as much as possible the distance between the electrodes 12 and the amplifiers 16.

The amplified EMGdi signals are sampled by a personal computer 19 through respective isolation amplifiers of a unit 18, to form signal segments of fixed duration. Unit 18 supplies electric power to the various electronic components of the differential and isolation amplifiers while ensuring adequate isolation of the patient's body from such power supply. The unit 18 also incorporates bandpass filters included in the respective EMGdi signal channels to eliminate the effects of aliasing. The successive EMGdi signal segments are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 31.

It is believed to be within the capacity of those of ordinary skill in the art to construct suitable differential amplifiers 16 and an adequate isolation amplifiers and power supply unit 18. Accordingly, the amplifiers 16 and the unit 18 will not be further described in the present specification.

Figure 4:
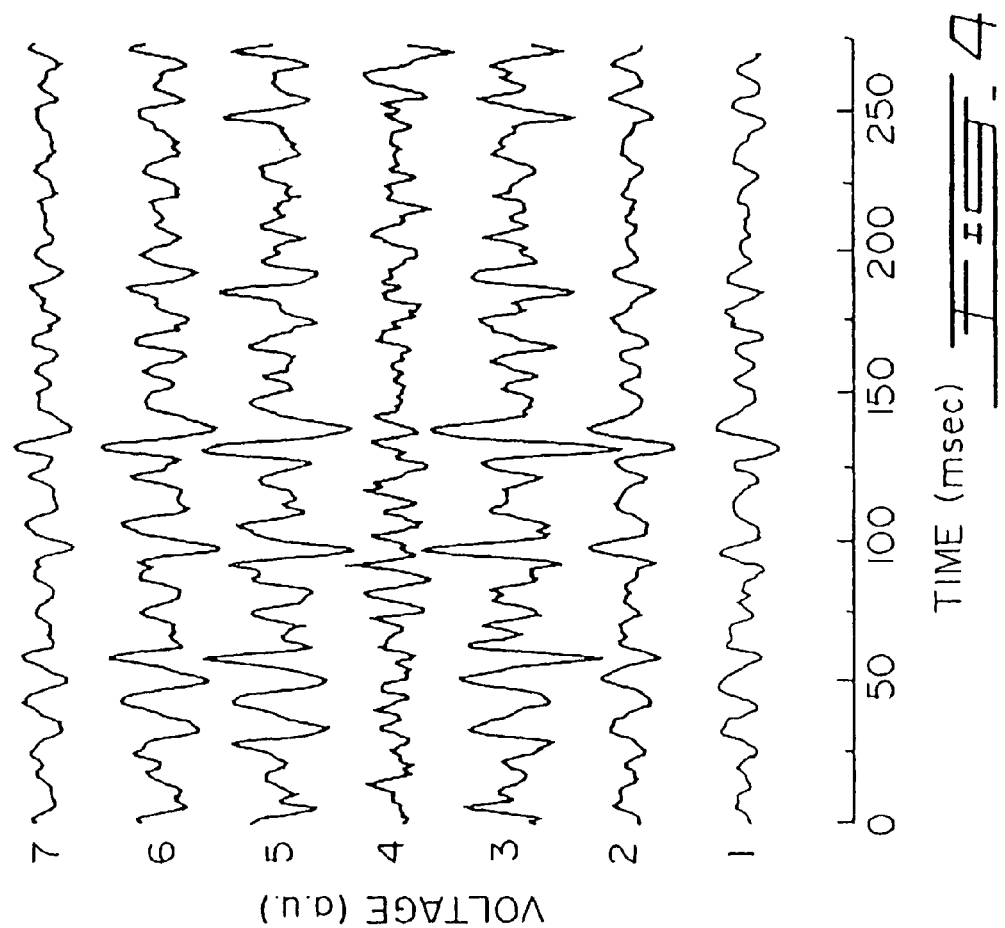
FIG. 4 is a graph showing a set of EMG signals of the diaphragm (EMGdi signals) detected by pairs of successive electrodes of the array of FIG. 2.

An example of the seven EMGdi signals collected by the pairs 1–7 of successive electrodes 12 (FIGS. 1 and 2) and supplied to the computer 19 is illustrated in FIG. 4.

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array.

The portion of the crural diaphragm 11 which forms the muscular tunnel through which the oesophageal catheter 13 is passed is referred to the "diaphragm depolarizing region" (DDR). The thickness of the DDR is 20–30 mm. It can be assumed that, within the DDR, the distribution of active muscle fibers has a center from which the majority of the EMGdi signals originate, i.e. the "diaphragm depolarizing region center" (DDR center). Therefore, EMGdi signals detected on opposite sides of the DDR center will be reversed in polarity with no phase shift; in other words, EMGdi signals obtained along the electrode array are reversing in polarity at the DDR center.

Moving centrally from the boundaries of the DDR, EMGdi power spectrums progressively attenuate and enhance in frequency. Reversal of signal polarity on either side of the electrode pair 4 with the most attenuated power spectrum confirms the position from which the EMGdi signals originate, the DDR center.

Referring to FIG. 5, the first task of the computer 19 is to determine the position of the center of the DDR along the array of electrodes 12. The center of the DDR is repeatedly determined at predetermined time intervals.

For that purpose, filtering step 505 removes from each EMGdi signal the motion artifacts, the electrocardiogram (ECG) component, and the disturbance from the electrical mains. Motion artifacts are induced by motion of the electrodes 12. More generally motion artifacts are defined as a low frequency fluctuation of the EMGdi signals' DC level induced by mechanical alterations of the electrode metal to electrolyte interface i.e. changes in electrode contact area and/or changes in pressure that the tissue exerts on the electrode.

In step 501, the filtered EMGdi signals from step 505 are cross-correlated in pairs. As well known to those of ordinary skill in the art, cross-correlation is a statistical determination of the phase relationship between two signals and essentially calculates the similarity between two signals in terms of a correlation coefficient r (step 502). A negative correlation coefficient r indicates that the cross-correlated signals are of opposite polarities.

FIG. 6 shows curves of the value of the correlation coefficient r versus the midpoint between the pairs of electrodes from which the correlated EMGdi signals originate. In this example, the inter-electrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 5 that negative correlation coefficients r are obtained when EMGdi signals from respective electrode pairs situated on opposite sides of the electrode pair 4 are cross-correlated. It therefore appears that the change in polarity occurs in the region of electrode pair 4, which is confirmed by the curves of FIG. 4. Accordingly, it can be assumed that the center of the DDR is situated substantially midway between the electrodes 12 forming pair 4.

For example, the center of the DDR can be precisely determined by interpolation (step 503 of FIG. 5) using a square law based fit of the three most negative correlation coefficients of curve 21 obtained by successive cross-correlation of the EMGdi signal segments from each electrode pair to the EMGdi signal segments from the second next electrode pair. Association of the center of the DDR to a pair of electrodes 12 provides a "reference position" from which to obtain EMGdi signal segments within the DDR. Such control is essential in overcoming the artifactual influence of perpendicular bipolar electrode filtering on the EMGdi power spectrum.

It has been experimentally demonstrated that EMGdi signals recorded in the oesophagus are satisfactory as long as they are obtained from electrode pairs (with an inter-electrode distance situated between 5 and 20 mm) positioned at a distance situated between 5 and 30 mm on the opposite sides of the DDR center (the inter-pair distance being therefore situated between 5 and 30 mm). Although EMGdi signals obtained from these positions offers a clear improvement in acceptance rate, the signal-to-noise ratio during quiet breathing still tends to remain unsatisfactorily low. The EMGdi signal obtained from one electrode pair (for example channel 0 in FIG. 7) situated in between the two electrode pairs used to produce the double subtracted signal, can be added to this double subtracted signal either before as a raw signal or after when RMS or equivalent EMGdi signal measure has been computed, in order to minimize loss of signal.

For example, in FIG. 4, the EMGdi signals originating from the electrode pairs 3 and 5 situated respectively 10 mm below and 10 mm above the DDR are strongly inversely correlated at zero time delay. In contrast to the inversely correlated EMGdi signals, the noise components for electrode pairs 3 and 5 are likely to be positively correlated. Hence, as illustrated in FIG. 7, subtraction of the EMGdi signals 24 and 25 from electrode pairs 3 and 5 will result into an addition of the corresponding EMGdi signals (signal 26 of FIG. 6) and into a subtraction, that is an elimination of the common noise components. This technique will be referred to as "the double subtraction technique" (step 504 of FIG. 5). Again, the EMGdi signal obtained from one electrode pair (for example channel 0 in FIG. 7) situated in between the two electrode pairs used to produce the double subtracted signal, can be added to this double subtracted signal either before as a raw signal or after when RMS or equivalent EMGdi signal measure has been computed, in order to minimize loss of signal.

Subtraction step 504 (second subtraction step of the double subtraction technique) can be carried out either in the time domain, or after conversion of signals 24 and 25 in the frequency domain. Double subtraction technique can be performed by subtracting other combinations of signals, for example by subtracting the EMGdi signal segments from electrode pair 2 from the EMGdi signal segments from electrode pair 5 (FIG. 4), by subtracting signal segments from electrode pair 6 from the signal segments from electrode pair 3 and by adding these differences, etc. What is important is to subtract two signals of opposite polarities obtained in the vicinity of the muscle. More than two signal pairs of opposite polarities can be used in the double subtraction. Again, the EMGdi signal obtained from one electrode pair (for example channel 0 in FIG. 7) situated in between the two electrode pairs used to produce the double subtracted signal, can be added to this double subtracted signal either before as a raw signal or after when RMS or equivalent EMGdi signal measure has been computed, in order to minimize loss of signal.

The double subtraction technique is carried out in step 504 on the pair of EMGdi signals (for example the signals from electrode pairs 3 and 6 shown in FIG. 4) identified in step 503 after appropriate filtering of these EMGdi signals in step 506. Still again, the EMGdi signal obtained from one electrode pair (for example channel 0 in FIG. 7) situated in between the two electrode pairs used to produce the double subtracted signal, can be added to this double subtracted signal either before as a raw signal or after when RMS or equivalent EMGdi signal measure has been computed, in order to minimize loss of signal.

Figure 8A:
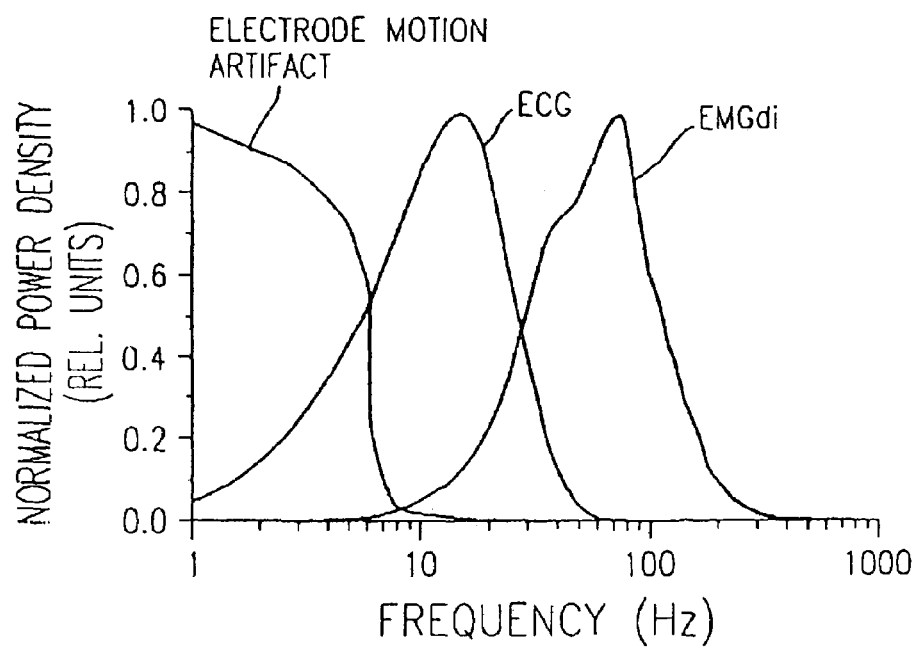
FIG. 8a is a graph showing the power density spectrum of electrode motion artifacts, the power density spectrum of ECG, and the power density spectrum of EMGdi signals.
Figure 8B:
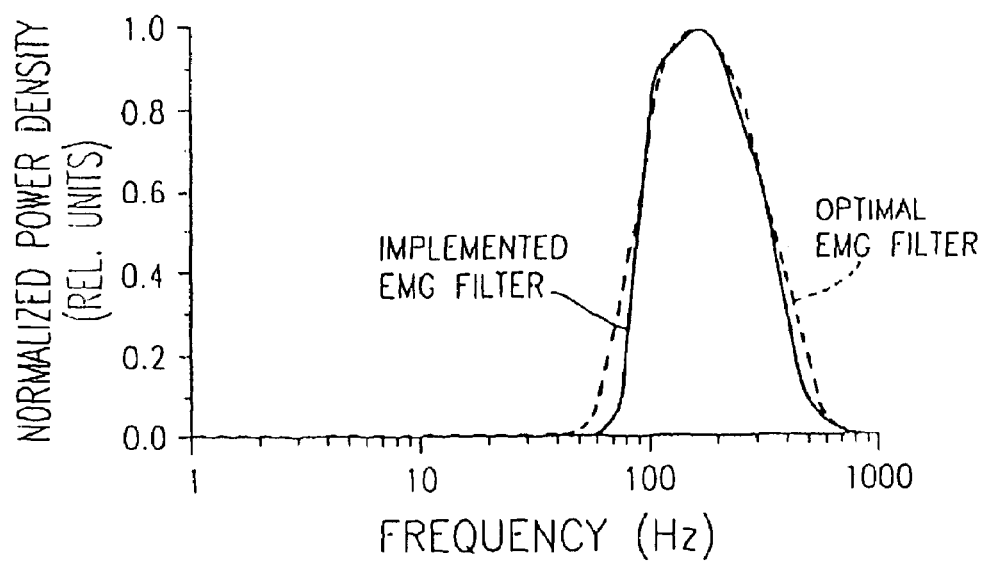
FIG. 8b is a graph showing an example of transfer function for a filter to be used for filtering out the electrode motion artifacts, ECG, and the 50 or 60 Hz disturbance from electrical mains.

The graph of FIG. 8a shows the power density spectrum of the above defined electrode motion artifacts, the power density spectrum of ECG, and the power density spectrum of EMGdi signals. The graph of FIG. 8b shows an example of transfer function for a filter (the dashed line showing the optimal transfer function, and the solid line the transfer function implemented by the inventors) to be used in step 505 for filtering out the electrode motion artifacts, ECG, and the 50 or 60 Hz disturbance from the electrical mains. Processing of the EMGdi signals by the computer 19 to follow as closely as possible the optimal transfer function of FIG. 8b will conduct adequately filtering step 505.

Therefore, double-subtracted signal segments 509 are obtained at the output of step 504 by subtracting the EMGdi signal segments from the pair of electrodes 12 in optimal location above the diaphragm from the EMGdi signal segments from the pair of electrodes 12 in optimal location below the diaphragm. More than two signal pairs of opposite polarities can be used in the double subtraction. Again, the EMGdi signal obtained from one electrode pair (for example channel 0 in FIG. 7) situated in between the two electrode pairs used to produce the double subtracted signal, can be added to this double subtracted signal either before as a raw signal or after when RMS or equivalent EMGdi signal measure has been computed, in order to minimize loss of signal.

Referring back to FIG. 5, step 506 calculates the RMS (root-mean-square) or equivalent or similar value 510 of the double-subtracted signal segments 509 produced in step 504. The increase in intensity obtained with the double subtraction technique is associated with a twofold increase in RMS values. RMS values obtained with the double subtraction technique are closely and linearly related to the original signals. It should be kept in mind that the RMS value can be replaced by any other value representative of the strength of the double-subtracted signal segments 509.

Figure 10:
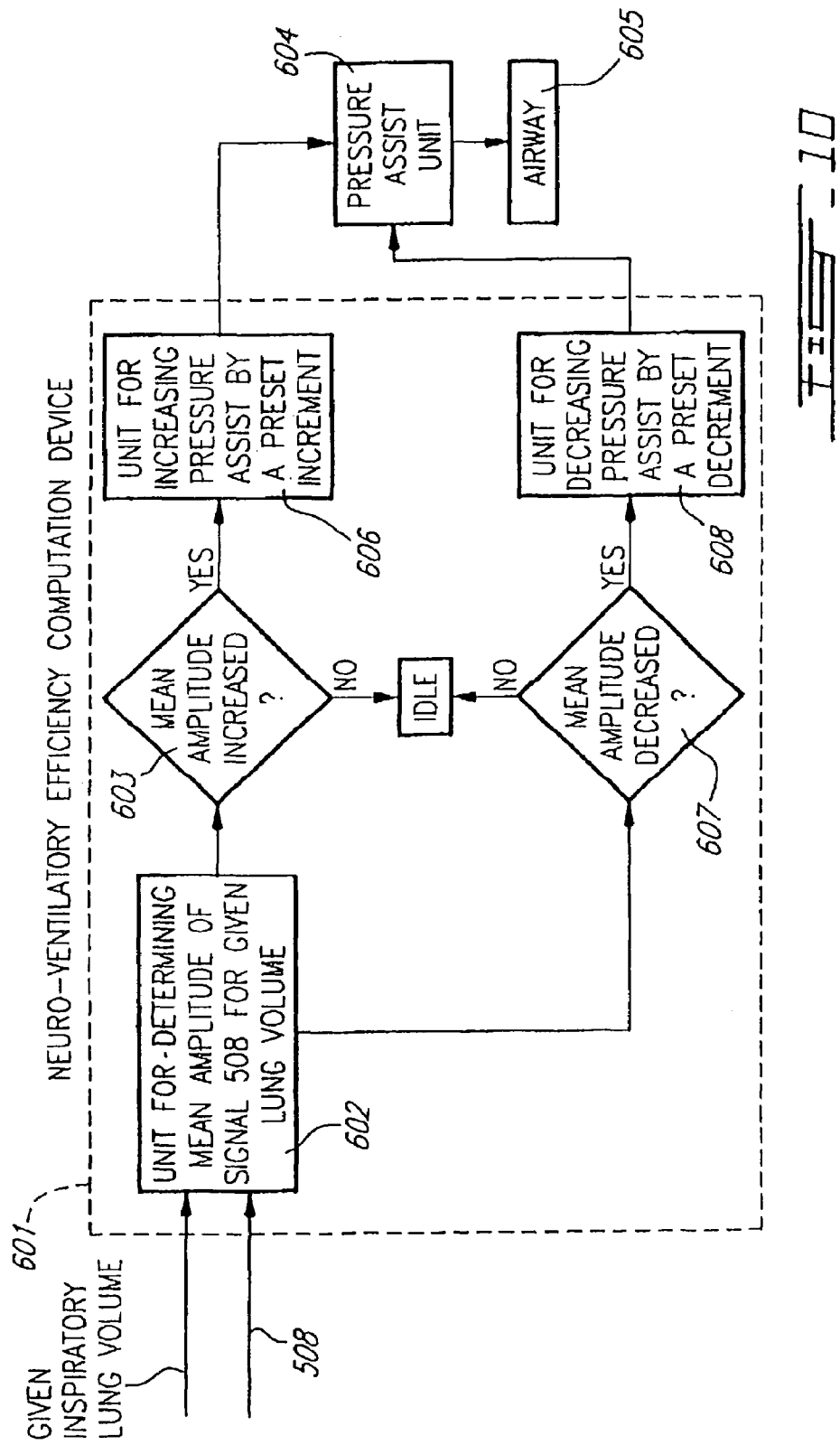
FIG. 10 is a schematic block diagram of a system according to the invention for controlling inspiratory assist by means of an EMGdi signal obtained with the above mentioned double subtraction technique and a measurement of the volume of air breathed by the patient by a commercially available system.

The digital RMS signal segment value 510 calculated by the computer 19 in step 506 is finally digital-to-analog converted to an on-line analog RMS value 508 (step 507) in view of controlling a lung ventilator 54 (FIG. 10). It should be mentioned that it is within the scope of the present invention to supply a digital value 608.

Figure 9:
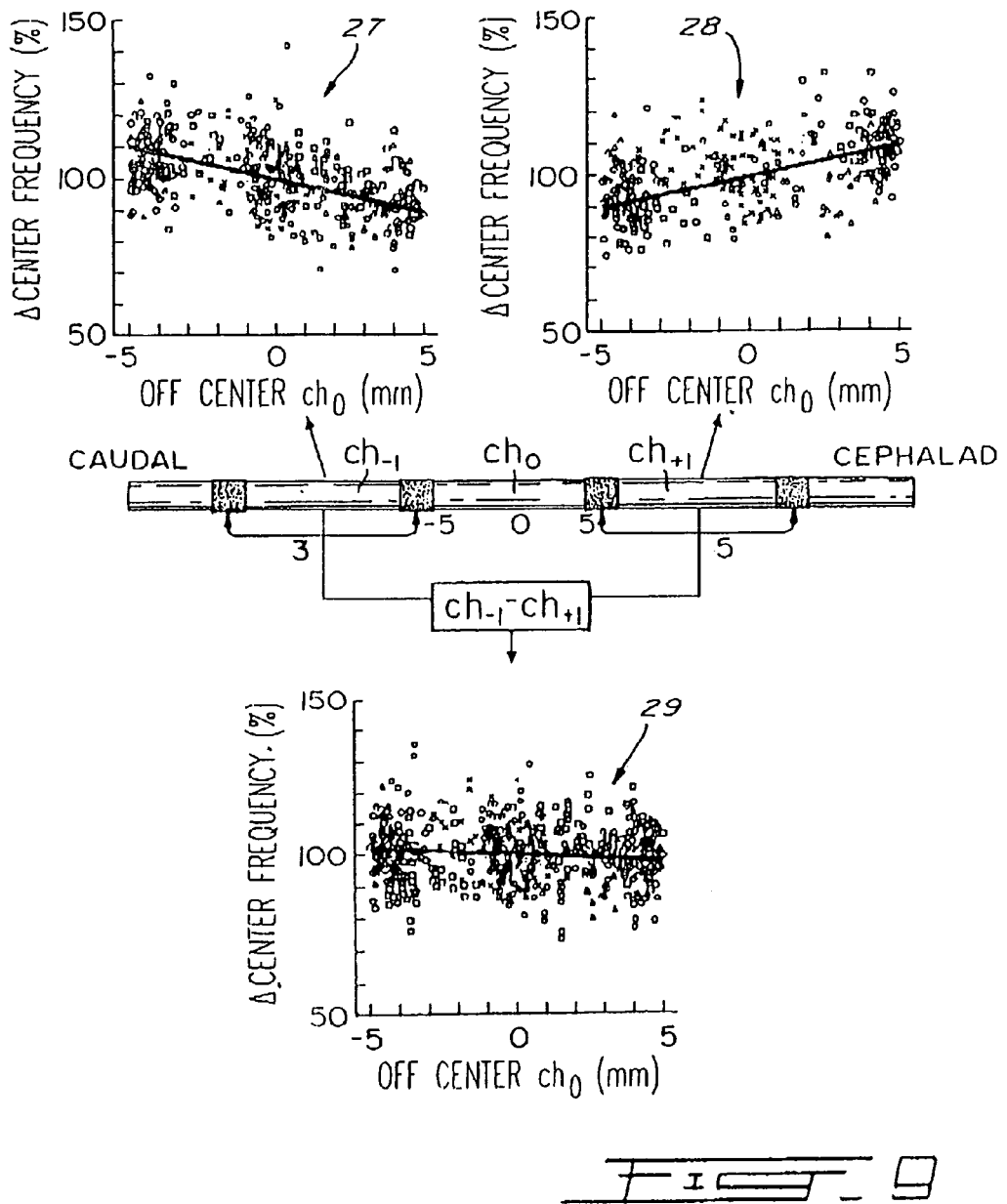
FIG. 9 is a schematic diagram illustrating in the frequency domain stabilization by the double subtraction technique of the center frequency upon displacement of the center of the depolarizing region of the diaphragm along the array of electrodes of FIG. 2.

The double subtraction technique compensates for the changes in signal strength and frequency caused by movement of the diaphragm 11 (FIG. 1) and/or the oesophagus during breathing of the patient 14 causing movement of the array of electrodes 12 with respect to the diaphragm 11. Referring to FIG. 9, off center of the array of electrodes 12 (electrode-position-induced filter effect) causes a variation of center frequency values due to filtering (see curves 27 and 28) for the EMGdi signals from the electrode pairs 3 and 5. The double subtraction technique eliminates such variation of center frequency values as indicated by curve 29 as well as variation of signal strength. Therefore, the reciprocal influence of the position of the DDR center on the EMGdi signal frequency content is eliminated by the double subtraction technique.

It has been found that the double subtraction technique may improve the signal-to-noise ratio by more than 2 dB and reduce an electrode-position-induced filter effect. Double subtraction technique is also responsible for a relative increase in acceptance rate by more than 30%.

Noise of non diaphragmatic origin or artifactual signals are strongly correlated at zero time delay and equal in polarity between all pairs of electrodes 12. Hence, this noise of non diaphragmatic origin or artifactual signals appear as a common mode signal for all electrode pairs and therefore, are substantially reduced by the double subtraction technique.

In the following description, it should be considered that the flow and volume of air breathed by the patient can be measured by any commercially available system.

Neuro-Ventilatory Efficiency;

The neuro-ventilatory efficiency is obtained by relating the diaphragm EMGdi signal intensity to changes in lung volume, or by relating the lung volume to changes in diaphragm EMGdi signal intensity. Since the relationship between the diaphragm EMGdi signal intensity and the lung volume is not linear, this non-linearity is minimized by expressing:

the intensity of the diaphragm EMGdi signal for a given volume change from end-expiratory lung volume, for example the EMGdi signal intensity obtained during 400 ml inspiration starting from end-expiratory lung volume (in the present disclosure, intensity is intended to encompass the mean, peak, median and total RMS intensity of the diaphragm EMGdi signal); or the lung volume obtained at a given diaphragm EMGdi signal intensity.

A relatively small tidal lung volume is suitable because the relationship between diaphragm EMGdi signal intensity and lung volume is relatively linear at this low range. Secondly, the use of a fixed, given tidal volume or diaphragm EMGdi signal intensity will protect against the non-linear influences and allows for a reliable estimation of relative changes in neuro-ventilatory efficiency.

In this manner, a ventilatory efficiency index expressing:

the EMGdi signal intensity for a given inspiratory lung volume starting from the end-expiratory lung volume; or the lung volume for a given diaphragm EMGdi signal intensity;

is calculated. If the EMGdi signal intensity for the above mentioned given inspiratory lung volume or the lung volume for the above mentioned given diaphragm EMGdi signal intensity is changing, the above indicated index will also change and this change can be expressed in percentage (%). For example, using the diaphragm EMGdi signal intensity for the above mentioned fixed, given inspiratory lung volume, an increased EMGdi signal intensity for the above mentioned given inspiratory lung volume will increase the index but will express a reduction in the neuro-ventilatory efficiency, and a decreased EMGdi signal intensity for that given inspiratory lung volume will reduce the index but will express an improvement of the neuro-ventilatory efficiency.

In the following description, an example using the EMGdi signal intensity for a fixed, given inspiratory lung volume will be given. However, it is within the scope of the present invention to use the lung volume for a fixed, given diaphragm EMGdi signal intensity.

Referring now to FIG. 10 a preferred, practical embodiment is described. A neuro-ventilatory efficiency computation device 601 receives the signal 508 of FIG. 5 as well as the given, fixed inspiratory lung volume. Device 601 comprises a unit 602 for determining the intensity of the signal 508 for the given inspiratory lung volume. Although it is not illustrated, it is within the scope of the present invention to calculate, in unit 602, the peak, mean, median or any other intensity measure of signal 508 for the given inspiratory lung volume. If the intensity of signal 508 for the given inspiratory lung volume has increased at least by a given percentage (step 603), i.e. the neuro-ventilatory efficiency index has increased at least by said given percentage, the pressure, flow, or volume assist unit 604 is controlled by a unit 606 in view of increasing the magnitude of the pressure assist to the patient by a preset increment until the intensity of the signal 608 for the given inspiratory lung volume is restored to a predetermined, preset value.

Still referring to FIG. 10, if the intensity for the given inspiratory lung volume has decreased at least by a given percentage (step 607), i.e. the neuro-ventilatory efficiency index has decreased at least by said given percentage, the pressure assist unit 604 is controlled by the unit 608 in view of decreasing the magnitude of the pressure assist by a preset increment until the intensity of the signal 508 for the given inspiratory lung volume is restored to the predetermined, preset value. Although it is not illustrated, it is within the scope of the present invention to calculate, in unit 602, the peak, mean, median or any other intensity measure of, signal 508 for the given inspiratory lung volume, instead of the intensity of this signal. Also, the signals at the outputs of the units 606 and 608 can be used to generate an alarm or to manually adjust the pressure, flow or volume assist to the patient.

The response time is adjustable. The time base used to calculate trends in the EMG intensity for a given volume or vice versa and used for the corrections is relatively slow (minutes) and the levels of applied support can be limited within a safe range. Again, an alarm can be generated or the pressure assist can be manually or automatically adjusted.

The pressure, flow, or volume assist unit 604 can be any device which can be controlled to generate any airway pressure of adjustable magnitude, for example any source of compressed gas, or a flow or volume pump. Of course, airway 605 refers to or, to the least, includes the patient's respiratory airway.

In this manner, the pressure assist unit 604 provides a pressure, flow, or volume assist that is adjusted in proportion to changed in neuro-ventilatory efficiency which is the EMGdi signal intensity at a given lung volume or vice versa. The pressure, flow, or volume assist unit continuoulsy operates to maintain a tracheal pressure, flow or volume that is adjusted in proportion to changes in neuro-ventilatory efficiency which is the EMGdi signal intensity at a given lung volume or vice versa.

Pre-Inspiratory Breathing Effort

A common problem with mechanically ventilated patients is that the patients' inspiratory effort will not immediately cause an inspiratory airflow so called "intrinsic PEEP" or "auto PEEP" which leads to a decrease in the neuro-ventilatory efficiency. The effect of "intrinsic PEEP" can be counteracted by the application of an "extrinsic PEEP". However, there are no easy applicable techniques to determine when the applied level of "extrinsic PEEP" is adequate. The level of pre-inspiratory effort obtained through the EMGdi signal intensity (common noise level subtracted) during for example a 100 milliseconds (ms) period immediately preceding the onset of inspiratory flow can be used to indicate the presence of "intrinsic PEEP", and the level of applied "extrinsic PEEP" can be adjusted such that the level of pre-inspiratory effort is suppressed i.e the EMGdi signal intensity (common noise level subtracted) during the above mentioned 100 ms period before onset of inspiratory flow is close to zero. A feedback loop can then be used to maintain the level of pre-inspiratory effort suppressed by adjusting as explained above the level of "extrinsic PEEP".

Figure 12A:
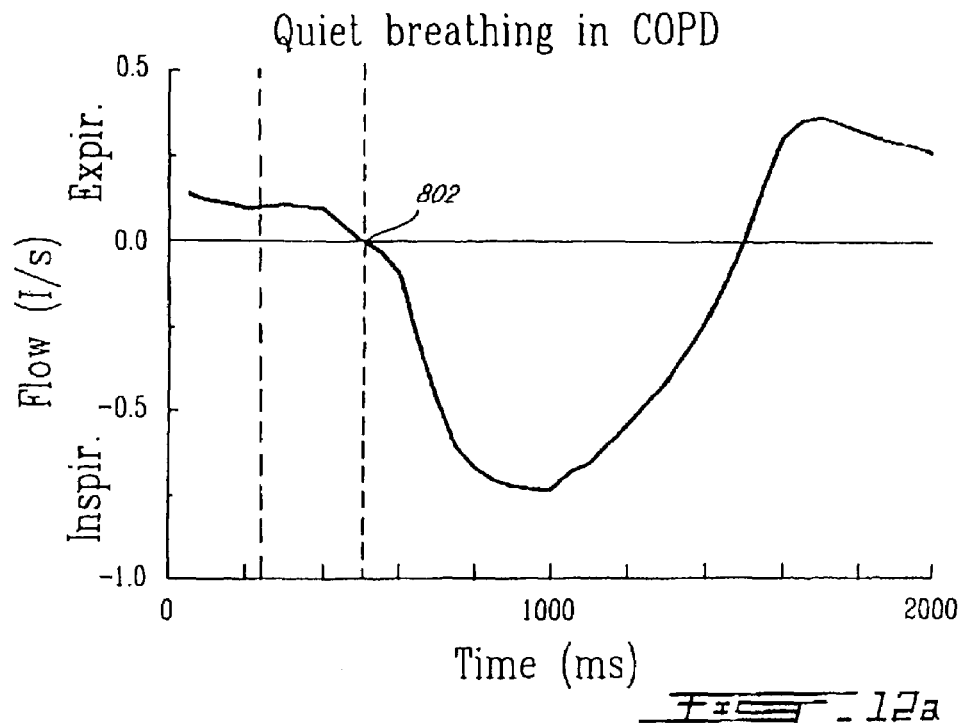
FIG. 12a is an exemplary graph of a patient's inspiratory flow versus time for quiet breathing in COPD (Chronic Obstructive Pulmonary Disease)

Just a word to mention that the above mentioned period of 100 ms can be replaced by a longer or shorter time period immediately preceding the onset of inspiratory flow or by the neuro-ventilatory delay 800 (FIG. 12*b*), i.e. the time period between the onset of EMG 801 (FIG. 12*b*) and the onset of inspiratory flow 802 (FIG. 12*a*).

Figure 11:
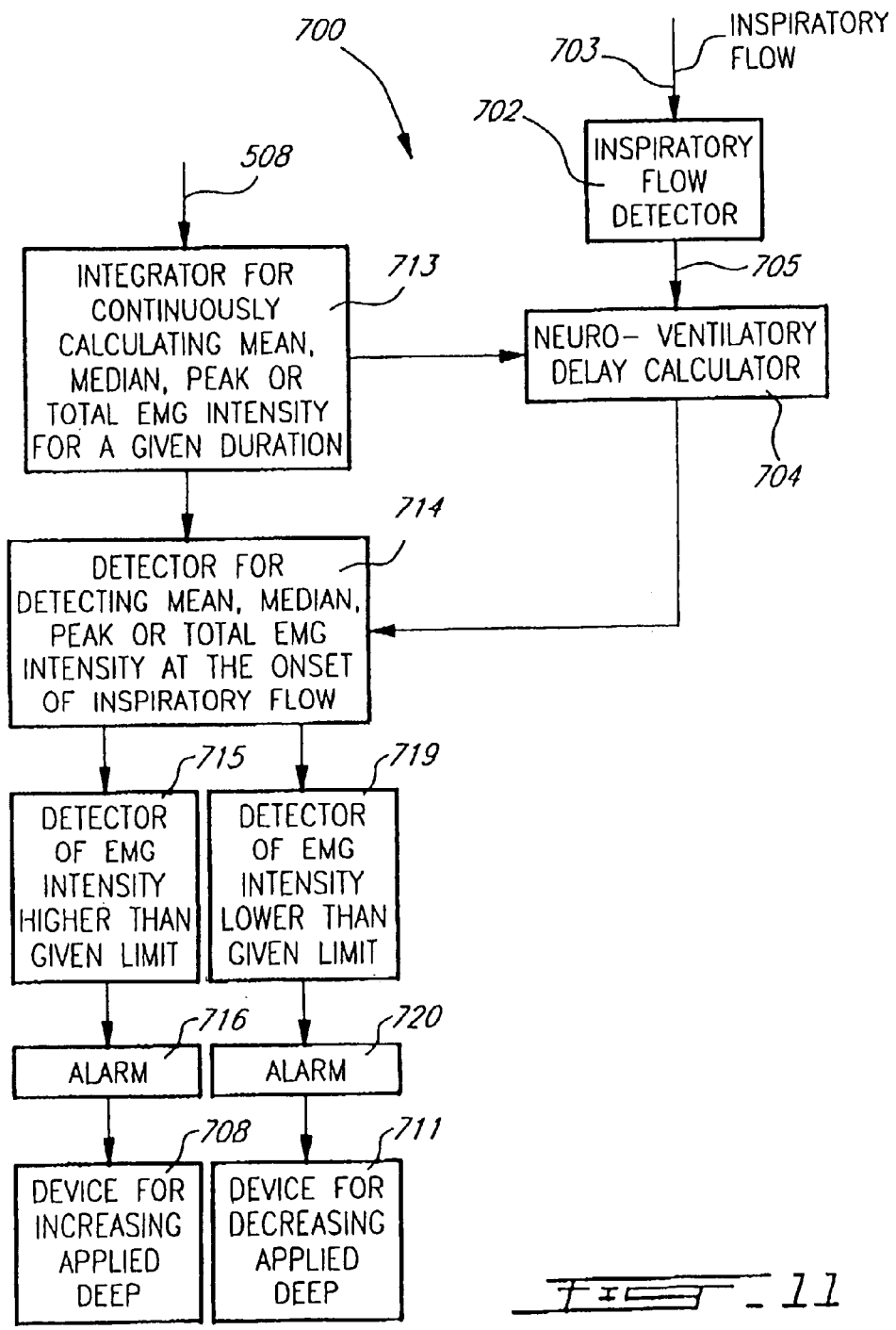
FIG. 11 is a schematic block diagram of a system according to the invention (a) capable to determine the time delay from the onset of EMG to the onset of inspiratory flow and (b) using the level of pre-inspiratory effort obtained through the EMGdi signal intensity (common noise level subtracted) during a predetermined time period immediately preceding the onset of inspiratory flow to indicate the presence of "intrinsic PEEP" and to adjust the level of applied "extrinsic PEEP" and/or ventilator trigger sensitivity such that the level of pre-inspiratory effort is suppressed, i.e the EMGdi signal intensity (common noise level subtracted) during the above mentioned predetermined time period is close to zero.

FIG. 11 of the appended drawings illustrates a preferred, practical embodiment 700.

In the embodiment 700, an integrator 713 is responsive to the RMS EMG signal 508 to continuously calculate the EMG intensity for the above mentioned 100 ms period or neuro-ventilatory delay 800.

Embodiment 700 also comprises an inspiratory flow detector 702 responsive to the patient's inspiratory flow 703 measured, as indicated in the foregoing description, through any commercially available system, to produce an output signal 705 representative of EMG activity.

Figure 12B:
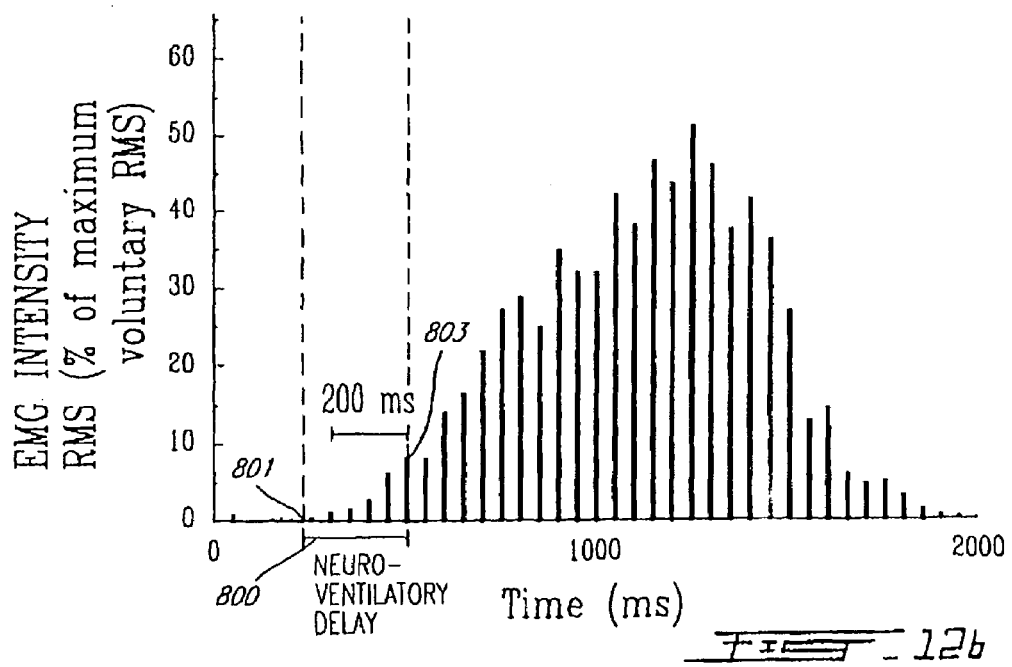
FIG. 12b is an exemplary graph of a patient's EMG RMS intensity versus time for quiet breathing in COPD.

The embodiment 700 of FIG. 11 also comprises a neuro-ventilatory delay calculator 704 responsive to (a) the detection of a RMS EMG signal intensity higher than the common noise level (5%), and (b) the detection of the onset of inspiratory flow by the detector 702 to calculate the neuro-ventilatory delay 800 (FIG. 12*b*).

A detector 714 is responsive to the EMG intensity calculated by the integrator 713 to detect the level of EMG intensity 803 (FIG. 12*b*) at the onset of inspiratory flow 802 (FIG. 12*a*) to trigger an alarm 716 when the level of the EMG intensity 803 at the onset of inspiratory flow 802 is higher than a given limit (detector 715). Upon triggering of the alarm 716, the level of applied "extrinsic PEEP" is either automatically or manually increased (device 708).

The detector 714 is responsive to the EMG intensity calculated by the integrator 713 to detect the level of EMG intensity 803 (FIG. 12*b*) at the onset of inspiratory flow 802 (FIG. 12*a*) to trigger an alarm 720 when the level of the EMG intensity 803 at the onset of inspiratory flow 802 is lower than a given limit (detector 719). Upon triggering of the alarm 720, the level of applied "extrinsic PEEP" is either automatically or manually decreased (device 711).

It should be mentioned that feedback from the neuro-ventilatory delay or pre-inspiratory EMG activity can also be used to adjust the sensitivity of the ventilators trigger functions.

Again, the time base used for these corrections is preferably relatively slow (minutes) and the levels of "extrinsic PEEP" can be limited within a safe range.

The pressure assist unit 604 can be any device which can be controlled to generate any airway flow and/or pressure of adjustable magnitude, for example any source of compressed gas, or a flow or volume pump.

In this manner, the delay from the beginning of the mechanically ventilated patients' inspiratory effort to the onset of the inspiratory assist will be minimized.

Although the present invention has been described hereinabove with reference to preferred embodiments thereof, these embodiments can be modified at will, within the scope of the appended claims, without departing from the spirit and nature of the subject invention.

What is claimed is:

1. A neuro-ventilatory efficiency computation method for monitoring/controlling a level of ventilatory assist to a patient comprising:
 receiving an EMG signal intensity representative of inspiratory effort of the patient
 receiving a lung volume value representative of a lung volume of the patient
 determining from the received EMG signal intensity and lung volume value at least one of the two following relations:
  an EMG signal intensity for a given lung volume value, the received lung volume value then being said given lung volume value; and
  a lung volume value for a given EMG signal intensity, the received EMG signal intensity then being said given EMG signal intensity; and
 increasing or decreasing the ventilatory assist level depending on whether said at least one relation has increased or decreased by at least a given percentage.

2. A neuro-ventilatory efficiency computation method as defined in claim 1, wherein:
 increasing or decreasing the ventilatory assist level comprises increasing the ventilatory assist level by a preset increment when said at least one relation has increased by at least said given percentage.

3. A neuro-ventilatory efficiency computation method as defined in claim 1, wherein:
 increasing or decreasing the ventilatory assist level comprises increasing the ventilatory assist level by a preset increment when said at least one relation has increased by at least said given percentage until the EMG signal intensity for the given lung volume value is restored to a predetermined, preset value.

4. A neuro-ventilatory efficiency computation method as defined in claim 1, wherein:
 increasing or decreasing the ventilatory assist level comprises decreasing the ventilatory assist level by a preset decrement when said at least one relation has decreased by at least said given percentage.

5. A neuro-ventilatory efficiency computation method as defined in claim 1, wherein:
 increasing or decreasing the ventilatory assist level comprises decreasing the ventilatory assist level by a preset decrement when said at least one relation has decreased by at least said given percentage until the EMG signal intensity for the given lung volume value is restored to a predetermined, preset value.

6. A neuro-ventilatory efficiency computation method as defined in claim 1, wherein increasing or decreasing the ventilatory assist level comprises:
 increasing the ventilatory assist level by a preset increment when said at least one relation has increased by at least said given percentage; and
 decreasing the ventilatory assist level by a preset decrement when said at least one relation has decreased by at least said given percentage.

7. A neuro-ventilatory efficiency computation method as defined in claim 1, further comprising:
 generating an alarm when said at least one relation has increased or decreased by the given percentage.

8. A neuro-ventilatory efficiency computation method as defined in claim 1, further comprising:
 manually adjusting the ventilatory assist level in response to a signal from the operation of increasing or decreasing the ventilatory assist level.

9. A neuro-ventilatory efficiency computation method as defined in claim 1, wherein:
 determining at least one relation comprises calculating one of the following values of the EMG signal intensity or lung volume value: a mean of the EMG signal intensity or lung volume value, a median the EMG signal intensity or lung volume value, and a peak the EMG signal intensity or lung volume value.

10. A neuro-ventilatory efficiency computation method as defined in claim 1, wherein the EMG signal intensity is a patient's diaphragm EMG signal intensity.

11. A neuro-ventilatory efficiency computation method as defined in claim 1, comprising:
 calculating a trend in the EMG signal intensity for a given lung volume value using an adjustable time base.

12. A neuro-ventilatory efficiency computation method as defined in claim 1, comprising:
 calculating a trend in the lung volume value for a given EMG signal intensity using an adjustable time base.

13. A neuro-ventilatory efficiency computation method as defined in claim 1, comprising:
 limiting a range of the ventilatory assist level within a safe range.

14. A neuro-ventilatory efficiency computation device for monitoring/controlling a level of ventilatory assist to a patient comprising:
 a first input for receiving an EMG signal intensity representative of inspiratory effort of the patient;
 a second input for receiving a lung volume value representative of a lung volume of the patient;
 connected to the first and second inputs a calculator of at least one of the two following relations:
  an EMG signal intensity for a given lung volume value, the lung volume value received on the second input then being said given lung volume value; and
  a lung volume value for a given EMG signal intensity, the EMG signal intensity received on the first input then being said given EMG signal intensity; and
 a controller connected to the first unit, the controller increasing or decreasing the ventilatory assist level depending on whether said at least one relation has increased or decreased by at least a given percentage.

15. A neuro-ventilatory efficiency computation device as defined in claim 14, wherein:
 the controller increases the ventilatory assist level by a preset increment when said at least one relation has increased by at least said given percentage.

16. A neuro-ventilatory efficiency computation device as defined in claim 14, wherein:
 the controller increases the ventilatory assist level by a preset increment when said at least one relation has increased by at least said given percentage until the EMG signal intensity for the given lung volume value is restored to a predetermined, preset value.

17. A neuro-ventilatory efficiency computation device as defined in claim 14, wherein:
 the controller decreases the ventilatory assist level by a preset decrement when said at least one relation has decreased by at least said given percentage.

18. A neuro-ventilatory efficiency computation device as defined in claim 14, wherein:
 the controller decreases the ventilatory assist level by a preset decrement when said at least one relation has decreased by at least said given percentage until the EMG signal intensity for the given lung volume value is restored to a predetermined, preset value.

19. A neuro-ventilatory efficiency computation device as defined in claim 14, wherein the controller:
   increases the ventilatory assist level by a preset increment when said at least one relation has decreased by at least said given percentage; and
   decreases the ventilatory assist level by a preset decrement when said at least one relation has decreased by at least said given percentage.

20. A neuro-ventilatory efficiency computation device as defined in claim 14, further comprising:
   an alarm generated when said at least one relation has increased or decreased by the given percentage.

21. A neuro-ventilatory efficiency computation device as defined in claim 14, further comprising:
   means for manually adjusting the ventilatory assist level.

22. A neuro-ventilatory efficiency computation device as defined in claim 14, wherein:
   the calculator determines one of the following values of the EMG signal intensity or lung volume value: a mean of the EMG signal intensity or lung volume value, a median the EMG signal intensity or lung volume value, and a peak the EMG signal intensity or lung volume value.

23. A neuro-ventilatory efficiency computation device as defined in claim 14, wherein the EMG signal intensity is a patient's diaphragm EMG signal intensity.

24. A neuro-ventilatory efficiency computation device as defined in claim 14, comprising:
   means for calculating a trend in the EMG signal intensity for a given lung volume value using an adjustable time base.

25. A neuro-ventilatory efficiency computation device as defined in claim 14, comprising:
   means for calculating a trend in the lung volume value for a given EMG signal intensity using an adjustable time base.

26. A neuro-ventilatory efficiency computation device as defined in claim 14, comprising:
   means for limiting a range of the ventilatory assist level within a safe range.

* * * * *